United States Patent [19]

Hedrich et al.

[11] 4,319,026
[45] Mar. 9, 1982

[54] HETEROCYCLIC-SUBSTITUTED HYDRAZIDES AND HYDRAZONES AS PLANT GROWTH REGULATORS

[75] Inventors: Loren W. Hedrich, Orange, Tex.; Natu R. Patel, Overland Park, Kans.; Joel L. Kirkpatrick, Washington Crossing, Pa.

[73] Assignee: Gulf Oil Corporation, Pittsburgh, Pa.

[21] Appl. No.: 178,241

[22] Filed: Aug. 14, 1980

[51] Int. Cl.$^3$ .................. C07D 277/62; C07D 277/20
[52] U.S. Cl. ................................ 542/419; 542/417; 548/198; 548/222; 548/233; 548/184; 71/90; 71/88; 548/185
[58] Field of Search ............... 548/194, 187, 198, 185, 548/184, 222, 233; 71/90, 88; 542/417, 419

[56] References Cited

U.S. PATENT DOCUMENTS

| | | | |
|---|---|---|---|
| 3,860,586 | 1/1975 | Kilbourn et al. | 548/194 |
| 4,025,528 | 5/1977 | Maeda et al. | 548/194 |
| 4,077,968 | 3/1978 | Maeda et al. | 544/194 |

*Primary Examiner*—Nicholas S. Rizzo
*Attorney, Agent, or Firm*—Deane E. Keith; Forfest D. Stine; Carl A. Cline

[57] ABSTRACT

A class of novel compounds is disclosed which has utility as plant growth regulators, having the general formula:

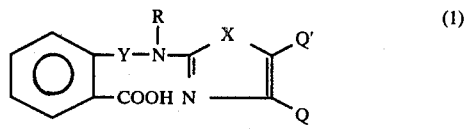

(1)

in which
X is O or S,
Y is one of the group:

—CONH—;

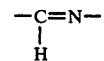

and

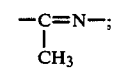

R is H or CH$_3$,
Q is phenyl or chlorophenyl when
Q' is hydrogen, or Q and Q' together may form the remainder of a benzene ring.

4 Claims, No Drawings

HETEROCYCLIC-SUBSTITUTED HYDRAZIDES AND HYDRAZONES AS PLANT GROWTH REGULATORS

DESCRIPTION OF THE INVENTION

Plant growth regulators are chemical compounds which have the ability to affect the physiological processes of plants, resulting in several types of observable effects, which may be classified as follows:

The auxin effect is a stimulation of cell elongation or enlargement. The cytokinin effect is observed as stimulation of cell division. The gibberellin effect is a stimulation of cell division or enlargement, or both. The effect of ethylene gas on growth is a stimulation of swelling or isodiametric growth of stems and roots. Besides these effects there are various growth regulators which inhibit a portion of, or a combination of physiological processes. Among the growth regulators are compunds which are produced naturally by the plants and are called plant hormones. Most of the natural plant hormones exhibit combinations of growth regulatory effects, which interact and overlap with other hormones. In general, the synthesis and use of the natural plant hormones to modify and improve the utility of crop plants is not successful because the resulting effects are not commercially desirable or are too complex and are beset with undesirable side effects. As a consequence, with few exceptions, the commercially useful growth regulators are compounds which are chemically unrelated to the naturally occurring hormones and exhibit the recognizable growth regulator effects in different and more useful combinations. There are now more than a score of such commercial growth regulators in extensive use in agriculture. However, many much-desired growth regulatory effects have not yet been achieved. Although growth regulation has been an active field of research for over fifty years, the fundamental mechanisms of the various types of growth regulatory action have not been elucidated. (See Chemical and Engineering News, Oct. 9, 1978, pages 18–26 and 31–34).

This invention is directed to a new class of growth regulators which exhibit a variety of useful effects, including increasing fruit set on annual crop plants of species such as *Lycopersicum esculentum*. This invention is also directed to methods of synthesis of the novel compounds and use of the compounds to regulate growth of plants.

Briefly, the novel growth regulators are compounds having the general structural formula:

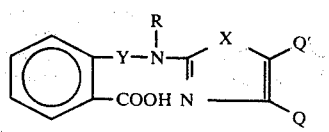

in which
X is O or S,
Y is one of the group:

—CONH—;

—C=N—
 |
 H and

—C=N—;
 |
 CH$_3$

R is H or CH$_3$,
Q is phenyl or chlorophenyl when
Q' is hydrogen, or Q and Q' together may form the remainder of a benzene ring.

Preferred compounds are those of the general structural formula:

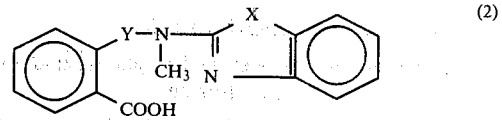

in which X is O or S and Y is

—CH=N— or —C—NH—.
             ‖
             O

The novel compounds may be made from available materials by means of the specific procedures which are exemplified below by way of illustration.

SYNTHESIS OF THE GROWTH REGULATOR COMPOUNDS

In the following examples, the synthesis of both the final compounds and principal intermediates is illustrated.

EXAMPLE 1

(a) Preparation of 2-(1-Methylhydrazino)benzoxazole Intermediate

To an ice cooled solution of 16.2 ml. of methylhydrazine in 100 ml. of dry ether is added 10.8 g. of 2-chlorobenzoxazole at a dropwise rate, keeping the temperature below 25° C. The mixture is stirred 30 min. in the ice bath and 2 hours at room temperature and then carefully evaporated. The residue is slurried with 200 ml. cold water, filtered, washed and dried to give 9.5 g. of 2-(1-methylhydrazine)benzoxazole, m.p. 128°–31°.

(b) Preparation of 1-(2-Carboxybenzoyl)-2-(benzoxazol-2-yl)-2-methylhydrazine

A suspension of 5.2 g. of phthalic anhydride in 75 ml. of chloroform is stirred and treated with 5.7 g. of 2-(1-methylhydrazino)benzoxazole. A clear yellow solution results and the temperature drops several degrees, then rises to 33+ C. After about 15 min. precipitation of a solid begins. An additional 200 ml. of chloroform is added and the mixture is stirred overnight. The solid is filtered, washed with chloroform and dried to give 8.6 g. of product, m.p. 140°–142°.

EXAMPLE 2

(a) Preparation of 2-(1-Methylhydrazino)benzothiazole Intermediate

To a stirred solution of 25.1 ml. of methylhydrazine in 100 ml. of dimethoxyethane immersed in an ice bath is slowly added a solution of 16.9 g. of 2-chlorobenzothiazole in 50 ml. of dimethoxyethane, maintaining the temperature below 30° C. After the addition is complete, the solution is stirred overnight at room temperature and then refluxed for 4 hours. Evaporation, slurrying the residue with 150 ml. of cold water, filtration and drying gives 17.6 g. of 2-(1-methylhydrazino)benzothiazole, m.p. 137°-9°.

(b) Preparation of 1-(2-Carboxybenzoyl)-2-(benzothiazol-2-yl)-2-methylhydrazine

Using the procedure described in Example 1, 5.2 g. of phthalic anhydride and 6.2 g. of 2-(1-methylhydrazino) benzothiazole gives 10.5 g. of product, m.p. 151°-3°.

EXAMPLE 3

(a) Preparation of 1-Methyl-1-(4-phenylthiazol-2-yl)hydrazine

A solution of 5.0 g. of 2-methyl-3-thiosemicarbazide and 7.3 g. of α-chloroacetophenone in 100 ml. of ethanol is heated at reflux for 4 hours and evaporated to dryness. The residue is taken up in a mixture of ethyl acetate and water and made basic with ammonium hydroxide.

The ethyl acetate phase is separated, dried over anhydrous sodium sulfate and evaporated, leaving 6.3 g. of 1-methyl-1-(4-phenyl-thiazol-2-yl)hydrazine as a heavy oil.

(b) Preparation of 1-(2-Carboxybenzoyl)-2-methyl-2-(4-phenylthiazol-2-yl)hydrazine A solution of 1.5 g. of phthalic anhydride and 2.0 g. of 1-methyl-1-(4-phenylthiazol-2-yl)hydrazine in 50 ml. of dimethylformamide is stirred for 16 hours. Addition of water precipitates a gummy solid which is taken up in ethyl acetate and the ethyl acetate solution is extracted with water, dried over anhydrous sodium sulfate and evaporated, giving a residue which is crystallized from ether/petroleum ether, yielding 0.6 g. of product, m.p. 122°-4°.

EXAMPLE 4

Preparation of 1-(2-Carboxybenzylidene)-2-(benzoxazol-2-yl)-2-methylhydrazine

To a stirred suspension of 1.6 g. of the benzoxazole intermediate product of Example 1 in 50 ml. of glacial acetic acid is added 1.5 g. of 2-carboxybenzaldehyde. After a few minutes the mixture becomes homogeneous, then quickly thickens as a new precipitate forms. Stirring is continued for 16 hours, water is added, and the solid is filtered, washed with water and dried to give 2.5 g. of product, m.p. 253°-5°.

Compounds which have been prepared by the above procedures are listed below in Table 1.

TABLE 1

| Comp'd. No. | Structural Formula | m.p. °C. | Comments on PGR Activity |
|---|---|---|---|
| 4222 | (structure) | 140–142° | Growth reduction |
| 4279 | (structure) | 122–4° | Growth reduction |
| 4297 | (structure) | 253–5° | Increase fruit set on *Lycopersicum esculentum* |
| 4298 | (structure) | 210–5° | Growth reduction |
| 4307 | (structure) | 151–3° | Increase fruit set on *Lycopersicum esculentum* |
| 4344 | (structure) | 197–8° | Growth reduction |
| 4416 | (structure) | 136–8° | Growth reduction |

USE OF THE GROWTH REGULATORS

In highly active compounds, phytotoxic and growth-altering effects of pre-emergent and post-emergent application are often readily apparent. These effects may be demonstrated by means of the following illustrative procedures.

PRE-EMERGENT APPLICATION

Disposable paper trays about 2½ inches deep were filled with soil and sprayed with aqueous spray mixtures at a rate of 5 lb. of active chemical per acre of sprayed area, were seeded with 6 species of plant seeds and were then covered with about ¼ inch of soil. The spray mixtures were prepared by dissolving the proper amount of growth regulator compound in 15 ml. of acetone, adding 4 ml. of a solvent-emulsifier consisting of 60 wt. percent of a commercial polyoxyethylated vegetable oil emulsifier (96 wt. percent active ingredient, Emulphor EL-719), 20 wt. percent xylene and 20 wt. percent deodorized kerosene, then bringing total volume up to 60 ml. by addition of warm water. Twenty-one days after seeding and treatment the plantings were examined and plant injury was rated according to the following schedule.

DEGREE OF EFFECT

0 = no effect
1 = slight effect, plants recovered
2 = moderate effect, injury to 26 to 75 percent
3 = severe effect, injury to 76 to 99 percent of foliage
4 = maximum effect (all plants died)

POST-EMERGENT APPLICATION

Several species of plants were grown in potting soil in disposable styrofoam trays and tomatoes were grown in four-inch pots in the greenhouse. Aqueous spray formulations were prepared and the growing plants were sprayed at a spray volume of 60 gallons per acre and an application rate of 5 lb. per acre. Spray mixtures were prepared in the manner described above. For comparative purposes, plants were also sprayed at 60 gal./acre with a spray mixture containing no growth regulant. Plant injury was again rated according to the schedule disclosed above.

Observations of growth regulator effects in both pre- and post-emergent tests were observed and recorded as follows:

| Effect | Abbreviations in Tables |
|---|---|
| Formative effect on new growth | F |
| Epinasty | E |
| Growth reduction | G |
| Necrosis | N |
| Non-emergence | K |
| Chlorosis | C |

In the table below there are tabulated the observations of pre- and post-emergent herbicidal and growth regulator effects resulting from use of the growth regulators of this invention according to the procedures set forth above.

TABLE 2

EFFECTS OF THE COMPOUNDS ON PLANT SPECIES

| Compound No. | Pre-emergent Effects | | | | | | Post-emergent Effects | | | | | |
|---|---|---|---|---|---|---|---|---|---|---|---|---|
| | Digitaria sanguinalis | Celosia plumosa | Bromus inermis | Setaria italica | Raphanus sativus | Beta vulgaris | Setaria italica | Medicago sativa | Avena sativa | Raphanus sativus | Beta vulgaris | Lycopersicum esculentum |
| 4222 | 0 | G1C1 | 0 | 0 | 0 | 0 | 0 | F1 | 0 | 0 | F1 | F1 |
| 4279 | 0 | 0 | 0 | 0 | 0 | 0 | 0 | F1 | — | F1 | F1 | 0 |
| 4297 | F1 | 0 | F1 | G1 | F1 | F1 | 0 | F2 | 0 | F1G1 | F2 | F2 |
| 4298 | 0 | — | F1 | 0 | 0 | F1 | 0 | F1 | 0 | F1 | N4 | F1 |
| 4307 | 0 | G1 | 0 | 0 | 0 | G1 | 0 | F1 | 0 | F1 | F1 | F3 |
| 4344 | 0 | 0 | 0 | 0 | 0 | 0 | 0 | 0 | 0 | F1G1 | F1 | F1 |
| 4416 | 0 | 0 | 0 | 0 | 0 | F1 | 0 | 0 | 0 | 0 | F1 | F1 |

The information presented in tabular form herein will enable a worker in the art to make a selection from among the growth regulator compounds of the invention and to make some judgment with regard to application rates, depending upon the effect which is desired. It may be seen, for example, that total kills of some species of vegetation frequently occurs at application rates as high as 5 to 10 lb. per acre, whereas beneficial effects may be observed on living plants at application rates 1 lb. per acre or less.

The growth regulator compounds are usually applied in combination with inert carriers or diluents, as in aqueous sprays, granules and dust formulations, in accordance with established practice in the art. An aqueous spray is usually prepared by mixing a wettable powder or emulsifiable concentrate formulation of a growth regulator with a relatively large amount of water to form a dispersion.

Wettable powders comprise intimate, finely divided mixtures of growth regulator compounds, inert solid carriers and surface active agents. The inert solid carrier is usually chosen from among the attapulgite clays, the kaolin clays, the montmorillonite clays, the diatomaceous earths, finely divided silica and purified silicates. Effective surfactants, which have wetting, penetrating and dispersing ability are usually present in a wettable powder formulation in proportions of from 0.5 to about 10 percent by weight. Among the surface active agents commonly used for this purpose are the sulfonated lignins, naphthalenesulfonates and condensed naphthalenesulfonates, alkylbenzenesulfonates, alkyl sulfates and non-ionic surfactants such as products of condensation of ethylene oxide with alkylphenols.

Emulsifiable concentrates of the growth regulator compunds comprise in each instance, a solution of growth regulator compound in a liquid carrier which is a mixture of water-immiscible solvent and surfactants, including emulsifiers. Useful solvents include aromatic hydrocarbon solvents such as the xylenes, alkylnaphthalenes, petroleum distillates, terpene solvents, ether-alcohols and organic ester solvents. Suitable emulsifiers, dispersing and wetting agents may be selected from the same classes of products which are employed in formulating wettable powders.

In general, the growth regulator formulations desirably contain from 0.1 percent to 95 percent by weight of a compound of formula (I) and from 0.1 to 75 percent of a carrier or surfactant. However, direct application to plant seeds prior to planting may be accomplished in some instances by mixing powdered solid growth regulator with seed to obtain a substantially uniform coating which is very thin and comprises only one or two percent by weight or less, based on the weight of the seed. In most instances, however, a nonphytotoxic solvent, such as methanol is employed as a carrier to facilitate the uniform distribution of growth regulator on the surface of the seed.

When a compound is to be applied to the soil, as for a pre-emergence application, granular formulations are sometimes more convenient than sprays. A typical granular formation comprises the growth regulator compound dispersed on an inert carrier such as coarsely ground clay, or clay which has been converted to granules by treatment of a rolling bed of the powdered material with a small amount of liquid in a granulating drum. In the usual process for preparing granular formulations, a solution of the active compound spray is sprayed on the granules while they are being agitated in a suitable mixing apparatus, after which the granules are dried with a current of air during continued agitation.

We claim:

1. Compounds of the formula:

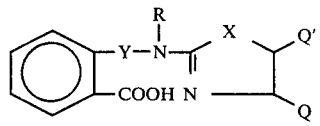

in which

X is O or S,
Y is —CONH—;

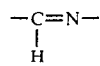

or

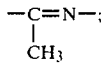

R is H or CH$_3$,
Q is phenyl or chlorophenyl when
Q' is hydrogen, or Q and Q' together may form the remainder of a benzene ring.

2. Compounds of the structural formula:

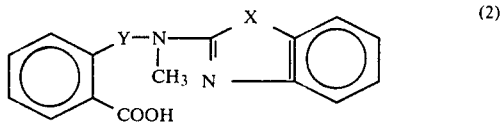

in which X is O or S and Y is

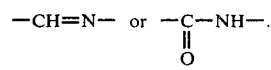

3. The compound according to claim 2 in which X is O and Y is —CH=N—.

4. The compound according to claim 2 in which X is S and Y is

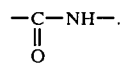

* * * * *